United States Patent
Lee et al.

(10) Patent No.: US 8,376,952 B2
(45) Date of Patent: Feb. 19, 2013

(54) METHOD AND APPARATUS FOR SENSING BLOOD OXYGEN

(75) Inventors: Hans C. Lee, Carmel, CA (US); Michael J. Lee, Carmel, CA (US)

(73) Assignee: The Nielsen Company (US), LLC., Schaumburg, IL (US)

( * ) Notice: Subject to any disclaimer, the term of this patent is extended or adjusted under 35 U.S.C. 154(b) by 1472 days.

(21) Appl. No.: 11/852,189

(22) Filed: Sep. 7, 2007

(65) Prior Publication Data
US 2009/0069652 A1 Mar. 12, 2009

(51) Int. Cl.
*A61B 5/08* (2006.01)
(52) U.S. Cl. ......... 600/484; 600/507; 600/500; 600/502
(58) Field of Classification Search .................. 600/483, 600/484, 493, 500, 502, 504, 507
See application file for complete search history.

(56) References Cited

U.S. PATENT DOCUMENTS

| | | |
|---|---|---|
| 4,695,879 A | 9/1987 | Weinblatt |
| 4,755,045 A | 7/1988 | Borah et al. |
| 4,846,190 A | 7/1989 | John |
| 4,931,934 A | 6/1990 | Snyder |
| 4,974,602 A | 12/1990 | Abraham-Fuchs et al. |
| 5,243,517 A | 9/1993 | Schmidt et al. |
| 5,406,957 A | 4/1995 | Tansey |
| 5,447,166 A | 9/1995 | Gevins |
| 5,450,855 A | 9/1995 | Rosenfeld |
| 5,579,774 A | 12/1996 | Miller et al. |
| 5,601,090 A | 2/1997 | Musha |
| 5,676,138 A | 10/1997 | Zawilinski |
| 5,692,906 A | 12/1997 | Corder |
| 5,724,987 A | 3/1998 | Gevins et al. |
| 5,740,812 A | 4/1998 | Cowan |
| 5,774,591 A | 6/1998 | Black et al. |
| 5,983,129 A | 11/1999 | Cowan et al. |
| 5,983,214 A | 11/1999 | Lang et al. |
| 6,099,319 A | 8/2000 | Zaltman et al. |
| 6,254,536 B1 | 7/2001 | DeVito |
| 6,292,688 B1 | 9/2001 | Patton |
| 6,309,342 B1 | 10/2001 | Blazey et al. |
| 6,322,368 B1 | 11/2001 | Young et al. |
| 6,330,378 B1 * | 12/2001 | Forrest et al. ................. 385/14 |
| 6,343,223 B1 * | 1/2002 | Chin et al. .................. 600/323 |
| 6,585,521 B1 | 7/2003 | Obrador |
| 6,623,428 B2 | 9/2003 | Miller et al. |

(Continued)

FOREIGN PATENT DOCUMENTS

| | | |
|---|---|---|
| KR | 10-2000-0072489 | 12/2000 |
| KR | 10-2001-0104579 | 11/2001 |

OTHER PUBLICATIONS

Form PCT/ISA/220, PCT/US07/15019, "PCT Notification of Transmittal of The International Search Report and the Written Opinion of the International Searching Authority, or the Declaration," 1 pg.

(Continued)

*Primary Examiner* — Michael Kahelin
*Assistant Examiner* — Tho Tran
(74) *Attorney, Agent, or Firm* — Hanley, Flight & Zimmerman, LLC (57) ABSTRACT

An exemplary embodiment providing one or more improvements includes a blood oxygen sensing apparatus and method in which an infra-red light is absorbed blood in portions that are related to levels of oxygen in the blood along a path.

44 Claims, 5 Drawing Sheets

U.S. PATENT DOCUMENTS

| | | |
|---|---|---|
| 6,626,676 B2 | 9/2003 | Freer |
| 6,652,283 B1 | 11/2003 | Van Schaack et al. |
| 6,656,116 B2 | 12/2003 | Kim et al. |
| 6,678,866 B1 | 1/2004 | Sugimoto et al. |
| 6,792,304 B1 | 9/2004 | Silberstein |
| 6,839,682 B1 | 1/2005 | Blume |
| 6,978,115 B2 | 12/2005 | Whitehurst et al. |
| 7,035,685 B2 | 4/2006 | Ryu et al. |
| 7,050,753 B2 | 5/2006 | Knutson |
| 7,113,916 B1 | 9/2006 | Hill |
| 7,328,053 B1* | 2/2008 | Diab et al. ............... 600/336 |
| D565,735 S | 4/2008 | Washbon |
| 7,920,919 B1* | 4/2011 | Nabutovsky ............... 607/19 |
| 2001/0016874 A1 | 8/2001 | Ono et al. |
| 2001/0056225 A1 | 12/2001 | DeVito |
| 2002/0154833 A1 | 10/2002 | Koch et al. |
| 2002/0182574 A1 | 12/2002 | Freer |
| 2003/0003433 A1 | 1/2003 | Carpenter et al. |
| 2003/0063780 A1 | 4/2003 | Gutta et al. |
| 2003/0076369 A1 | 4/2003 | Resner |
| 2003/0081834 A1 | 5/2003 | Philomin et al. |
| 2003/0093784 A1 | 5/2003 | Dimitrova et al. |
| 2003/0126593 A1 | 7/2003 | Mault |
| 2003/0153841 A1 | 8/2003 | Kilborn et al. |
| 2004/0018476 A1 | 1/2004 | Ladue |
| 2004/0039268 A1 | 2/2004 | Barbour et al. |
| 2004/0072133 A1 | 4/2004 | Kullok et al. |
| 2004/0208496 A1 | 10/2004 | Pilu |
| 2004/0267141 A1 | 12/2004 | Amano et al. |
| 2005/0008197 A1* | 1/2005 | Dennis ............... 382/115 |
| 2005/0010087 A1 | 1/2005 | Banet |
| 2005/0043774 A1 | 2/2005 | Devlin et al. |
| 2005/0045189 A1 | 3/2005 | Jay |
| 2005/0066307 A1 | 3/2005 | Patel et al. |
| 2005/0071865 A1 | 3/2005 | Martins |
| 2005/0097594 A1 | 5/2005 | O'Donnell et al. |
| 2005/0113656 A1 | 5/2005 | Chance |
| 2005/0172311 A1 | 8/2005 | Hjelt et al. |
| 2005/0250997 A1* | 11/2005 | Takeda et al. ............... 600/310 |
| 2006/0161056 A1* | 7/2006 | Diab et al. ............... 600/336 |
| 2006/0206019 A1* | 9/2006 | Zhang et al. ............... 600/323 |
| 2006/0258926 A1 | 11/2006 | Ali et al. |
| 2006/0264721 A1* | 11/2006 | Petersen et al. ............... 600/336 |
| 2006/0277102 A1 | 12/2006 | Agliozzo |
| 2006/0293921 A1 | 12/2006 | McCarthy et al. |
| 2007/0053513 A1 | 3/2007 | Hoffberg |
| 2007/0055169 A1 | 3/2007 | Lee et al. |
| 2007/0060830 A1 | 3/2007 | Le et al. |
| 2007/0060831 A1 | 3/2007 | Le et al. |
| 2007/0066914 A1 | 3/2007 | Le et al. |
| 2007/0116037 A1 | 5/2007 | Moore |
| 2007/0168461 A1 | 7/2007 | Moore |
| 2007/0173733 A1 | 7/2007 | Le et al. |
| 2007/0179396 A1 | 8/2007 | Le et al. |
| 2007/0184420 A1 | 8/2007 | Mathan et al. |
| 2007/0208240 A1* | 9/2007 | Nordstrom et al. ............... 600/323 |
| 2007/0225585 A1 | 9/2007 | Washbon et al. |
| 2007/0235716 A1 | 10/2007 | Delic et al. |
| 2007/0238945 A1 | 10/2007 | Delic et al. |
| 2007/0265507 A1 | 11/2007 | De Lemos |
| 2008/0091512 A1 | 4/2008 | Marci et al. |
| 2008/0144882 A1 | 6/2008 | Leinbach et al. |
| 2008/0159365 A1 | 7/2008 | Dubocanin et al. |
| 2008/0177197 A1 | 7/2008 | Lee et al. |
| 2008/0211768 A1 | 9/2008 | Breen et al. |
| 2008/0214943 A1* | 9/2008 | Kara et al. ............... 600/504 |
| 2008/0218472 A1 | 9/2008 | Breen et al. |
| 2009/0024049 A1 | 1/2009 | Pradeep et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0025023 A1 | 1/2009 | Pradeep et al. |
| 2009/0030287 A1 | 1/2009 | Pradeep et al. |
| 2009/0030303 A1 | 1/2009 | Pradeep et al. |
| 2009/0030717 A1 | 1/2009 | Pradeep et al. |
| 2009/0030930 A1 | 1/2009 | Pradeep et al. |
| 2009/0036755 A1 | 2/2009 | Pradeep et al. |
| 2009/0036756 A1 | 2/2009 | Pradeep et al. |
| 2009/0062629 A1 | 3/2009 | Pradeep et al. |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0082643 A1 | 3/2009 | Pradeep et al. |
| 2009/0083129 A1 | 3/2009 | Pradeep et al. |
| 2009/0105576 A1 | 4/2009 | Do et al. |
| 2009/0112077 A1 | 4/2009 | Nguyen et al. |
| 2009/0156925 A1 | 6/2009 | Jin et al. |
| 2009/0163784 A1* | 6/2009 | Sarpeshkar et al. .......... 600/322 |
| 2009/0214060 A1 | 8/2009 | Chuang et al. |
| 2009/0222330 A1 | 9/2009 | Leinbach |

OTHER PUBLICATIONS

Form PCT/ISA/210, PCT/US07/15019, "PCT International Search Report," 2 pgs.

Form PCT/ISA/237, PCT/US07/15019, "PCT Written Opinion of the International Searching Authority," 5 pgs.

Form PCT/IB/326, PCT/US07/015019, "Notification Concerning Transmittal of International Preliminary Report on Patentability."

Form PCT/IB/373, PCT/US07/15019, "International Preliminary Report on Patentability."

Form PCT/ISA/220, PCT/US07/14955, "PCT Notification of Transmittal of The International Search Report and the Written Opinion of the International Searching Authority, or the Declaration," 1 pg.

Form PCT/ISA/210, PCT/US07/14955, "PCT International Search Report," 2 pgs.

Form PCT/ISA/237, PCT/US07/14955, "PCT Written Opinion of the International Searching Authority," 6 pgs.

Form PCT/IB/326, PCT/US07/14955, "Notification Concerning Transmittal of International Preliminary Report on Patentability." 1 page.

Form PCT/IB/373,•PCT/US07/14955, "International Preliminary Report on Patentability." 1 page.

Form PCT/ISA/220, PCT/US07/16796, "PCT Notification of Transmittal of The International Search Report and the Written Opinion of the International Searching Authority, or the Declaration," 1 pg.

Form PCT/ISA/210, PCT/US07/16796, "PCT International Search Report," 2 pgs.

Form PCT/ISA/237, PCT/US07/16796, "PCT Written Opinion of the International Searching Authority," 6 pgs.

Form PCT/IB/326, PCT/US07/16796, "Notification Concerning Transmittal of International Preliminary Report on Patentability." 1 page.

Form PCT/IB/373, PCT/US07/16796, "International Preliminary Report on Patentability." 1 page.

Form PCT/ISA/220, PCT/US06/31569, "PCT Notification of Transmittal of The International Search Report and the Written Opinion of the International Searching Authority, or the Declaration," 1 pg.

Form PCT/ISA/210, PCT/US06/31569, "PCT International Search Report," 3 pgs.

Form PCT/ISA/237, PCT/US06/31569, "PCT Written Opinion of the International Searching Authority," 6 pgs.

Form PCT/IB/326, PCT/US06/31569, "Notification Concerning Transmittal of International Preliminary Report on Patentability." 1 page.

Form PCT/IB/373, PCT/US06/31569, "International Preliminary Report on Patentability." 1 page.

Form PCT/ISA/220, PCT/US07/20714, "PCT Notification of Transmittal of The International Search Report and the Written Opinion of the International Searching Authority, or the Declaration," 1 pg.

Form PCT/ISA/210, PCT/US07/20714, "PCT International Search Report," 2 pgs.

Form PCT/ISA/237, PCT/US07/20714, "PCT Written Opinion of the International Searching Authority," 6 pgs.

Form PCT/IB/326, PCT/US07/20714, "Notification Concerning Transmittal of International Preliminary Report on Patentability." 1 page.

Form PCT/IB/373, PCT/US07/20714, "International Preliminary Report on Patentability." 1 page.

Form PCT/ISA/220, PCT/US07/17764, "PCT Notification of Transmittal of The International Search Report and the Written Opinion of the International Searching Authority, or the Declaration," 1 pg.
Form PCT/ISA/210, PCT/US07/17764, "PCT International Search Report," 2 pgs.
Form PCT/ISA/237, PCT/US07/17764, "PCT Written Opinion of the International Searching Authority," 7 pgs.
Form PCT/IB/326, PCT/US07/17764, "Notification Concerning Transmittal of International Preliminary Report on Patentability." 1 page.
Form PCT/IB/373, PCT/US07/17764, "International Preliminary Report on Patentability." 1 page.
Form PCT/ISA/220, PCT/US07/20713, "PCT Notification of Transmittal of The International Search Report and the Written Opinion of the International Searching Authority, or the Declaration," 1 pg.
Form PCT/ISA/210, PCT/US07/20713, "PCT International Search Report," 2 pgs.
Form PCT/ISA/237, PCT/US07/20713, "PCT Written Opinion of the International Searching Authority," 5 pgs.
Form PCT/IB/326, PCT/US07/20713, "Notification Concerning Transmittal of International Preliminary Report on Patentability." 1 page.
Form PCT/IB/373, PCT/US07/20713, "International Preliminary Report on Patentability." 1 page.
Form PCT/ISA/220, PCT/US08/09110, "PCT Notification of Transmittal of The International Search Report and the Written Opinion of the International Searching Authority, or the Declaration," 1 pg.
Form PCT/ISA/210, PCT/US08/09110, "PCT International Search Report," 3 pgs.
Form PCT/ISA/237, PCT/US08/09110, "PCT Written Opinion of the International Searching Authority," 4 pgs.
Form PCT/ISA/220, PCT/US08/75640, "PCT Notification of Transmittal of The International Search Report and the Written Opinion of the International Searching Authority, or the Declaration," 1 pg.
Form PCT/ISA/210, PCT/US08/75640, "PCT International Search Report," 2 pgs.
Form PCT/ISA/237, PCT/US08/75640, "PCT Written Opinion of the International Searching Authority," 3 pgs.
Form PCT/ISA/220, PCT/US08/78633, "PCT Notification of Transmittal of The International Search Report and the Written Opinion of the International Searching Authority, or the Declaration," 1 pg.
Form PCT/ISA/210, PCT/US08/78633, "PCT International Search Report," 2 pgs.
Form PCT/ISA/237, PCT/US08/78633, "PCT Written Opinion of the International Searching Authority," 6 pgs.
Form PCT/ISA/220, PCT/US08/82147, "PCT Notification of Transmittal of The International Search Report and the Written Opinion of the International Searching Authority, or the Declaration," 1 pg.
Form PCT/ISA/210, PCT/US08/82147, "PCT International Search Report," 2 pgs.
Form PCT/ISA/237, PCT/US08/82147, "PCT Written Opinion of the International Searching Authority," 13 pgs.
Form PCT/ISA/220, PCT/US08/82149, "PCT Notification of Transmittal of The International Search Report and the Written Opinion of the International Searching Authority, or the Declaration," 1 pg.
Form PCT/ISA/210, PCT/US08/82149, "PCT International Search Report," 2 pgs.
Form PCT/ISA/237, PCT/US08/82149, "PCT Written Opinion of the International Searching Authority," 14 pgs.
Form PCT/ISA/220, PCT/US08/75651, "PCT Notification of Transmittal of The International Search Report and the Written Opinion of the International Searching Authority, or the Declaration," 1 pg.
Form PCT/ISA/210, PCT/US08/75651, "PCT International Search Report," 2 pgs.
Form PCT/ISA/237, PCT/US08/75651, "PCT Written Opinion of the International Searching Authority," 9 pgs.
Form PCT/ISA/220, PCT/US08/85723, "PCT Notification of Transmittal of The International Search Report and the Written Opinion of the International Searching Authority, or the Declaration," 1 pg.
Form PCT/ISA/210, PCT/US08/85723, "PCT International Search Report," 2 pgs.
Form PCT/ISA/237, PCT/US08/85723, "PCT Written Opinion of the International Searching Authority," 7 pgs.
Form PCT/ISA/220, PCT/US08/85203, "PCT Notification of Transmittal of The International Search Report and the Written Opinion of the International Searching Authority, or the Declaration," 1 pg.
Form PCT/ISA/210, PCT/US08/85203, "PCT International Search Report," 2 pgs.
Form PCT/ISA/237, PCT/US08/85203, "PCT Written Opinion of the International Searching Authority," 6 pgs.
Form PCT/ISA/220, PCT/US08/75649, "PCT Notification of Transmittal of The International Search Report and the Written Opinion of the International Searching Authority, or the Declaration," 1 pg.
Form PCT/ISA/210, PCT/US08/75649, "PCT International Search Report," 3 pgs.
Form PCT/ISA/237, PCT/US08/75649, "PCT Written Opinion of the International Searching Authority," 5 pgs.
Technology Platform: SmartShirt + Eye-Tracking Innerscope Research, Mar. 2007.
Egner, Tobias; Emilie Strawson, and John H. Gruzelier, "EEG Signature and Phenomenology of Alpha/theta Neurofeedback Training Versus Mock Feedback." Applied Psychophysiology and Biofeedback. vol. 27, No. 4. Dec. 2002.
Clarke, Adam R. et al., EEG Analysis of Children with Attention-Deficit/Hyperactivity Disorder and Comorbid Reading Disabilities, Journal of Learning Disabilities, vol. 35, No. 3, (May-Jun. 2002), pp. 276-285.
Carter, R., "Mapping the Mind" 1998 p. 182 University of California Press, Berkley.
Harmony et al. (2004) Specific EEG frequencies signal general common cognitive processes as well as specific tasks processes in man. Int. Journal of Psychophysiology 53(3): 207-16.
Klimesch, W., Schimke, H., Schwaiger, J. (1994) Episodic and semantic memory: an analysis in the EEG theta and alpha band. Electroencephalography Clinical Neurophysiology.
Mizuhara, H.,Wang LQ, Kobayashi, K., Yamaguchi, Y., (2004) A long range cortical network emerging with theta oscillation in mental task. Neuroreport 15(8): 1233-1238.
Selden, G (1981) "Machines that Read Minds." Science Digest, October.
Willis, M. & Hodson, V.; Discover Your Child's Learning Style: Children Learn in Unique Ways—Here's the Key to Every Child's Learning Success, Prime Publishing. Roseville, CA.
Wise, A (1996) The High Performance Mind, Mastering Brainwaves for Insight, Healing and Creativity. G.P. Putnam's Son, New York. pp. 13-15; 20-22; 143-156.
Wise, A (1996) The High Performance Mind, Mastering Brainwaves for Insight, Healing and Creativity. G.P. Putnam's Son, New York. pp. 156-158; 165-170; 186-187, 189-192.
El-Bab, M. (2001) Cognitive event related potentials during a learning task. Doctoral Dissertation, Faculty of Medicine, University of Southampton, UK.
Gevins et al. (1997) High resolution EEG mapping of cortical activation related to a working memory, Cereb Cortex. 7: 374-385.
Hughes, J.R. & John, E.R. (1999) Conventional and Quantitative Electroencephalography in Psychiatry. Journal of Neuropsychiatry and Clinical Neurosciences. vol. 11(2): 190-208.

* cited by examiner

METHOD AND APPARATUS FOR SENSING BLOOD OXYGEN

BACKGROUND

Blood oxygen sensors have been used in the medical field for many years. These sensors are used for determining heart rate and blood oxygen levels of a person in a hospital or clinical setting. Pulse rate, oxygenation levels and/or other information determined by the sensor are typically displayed on a monitor for healthcare professional or other individual to view and evaluate to determine the person's health.

Blood oxygen sensors are typically attached to the person by clipping to the person's ear, or by slipping onto a person's finger. Conventional sensors measure the blood oxygen by measuring the difference in absorption of light at two different wavelengths. The blood oxygen level in these sensors is determined based on a ratio of absorbance of the two different wavelengths. Pulse rate is determined using the changes in blood oxygen level over an interval of time.

Conventional blood oxygen sensors have several drawbacks which can cause the sensors to produce results that are inaccurate, or in some instances may prevent the sensors from producing results at all. One of these drawbacks is caused by interference from other light sources. Light from these other sources can interfere with the detection of the two wavelengths and can distort the ratios of the two wavelengths, leading to inaccurate results in blood oxygen levels.

Other light sources can be the sun, interior lighting such as fluorescent and incandescent lights and other sources. These sources add light to the sensor which is unrelated to the oxygen levels in the blood of the person. This additional light can cause difficulties in distinguishing between light levels that are related to the blood oxygen content and light levels that are unrelated. The additional light is considered to be unwanted noise.

Another source of inaccuracy in traditional sensors is a result of movement of the person and the sensor during use. Movement can cause variations in amplitude of the additional light sources which can interfere with the operation of the blood oxygen sensor.

Traditional blood oxygen sensors use a system in which the two wavelengths of light pass through the tissue in a limited path. The path in the ear mounted device usually consists of the light passing straight through the tissue of the earlobe where a detector then detects the light. Other types of devices detect a reflection of the light. In either case, the light path through the tissue is limited and the light may miss substantial blood flow, thereby making inaccurate or non-existent readings. These devices also have a limited resolution to pick up and extract secondary signals that are related to blood oxygen levels, such as breathing.

Another issue involves the optical detectors used in traditional sensors. These sensors tend to produce a non-linear response at the lower light levels encountered when detecting blood oxygen levels. This non-linear response can make it difficult to determine characteristics of the blood oxygen levels that are represented in the lower light levels.

The foregoing examples of the related art and limitations related therewith are intended to be illustrative and not exclusive. Other limitations of the related art will become apparent to those of skill in the art upon reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In general, a blood oxygen sensing apparatus and method are described for use in determining circulatory related characteristics of a person. In one embodiment, an oscillating light is generated having an intensity that oscillates at an oscillating light frequency. The oscillating light includes an electromagnetic wavelength which causes the oscillating light to be absorbed by some tissue of the person in amounts that are proportional to a volume of oxygenated blood in the tissue of the person. The oscillating light is directed towards the tissue of the person to cause the oscillating light to enter the tissue and pass through the tissue. The oscillating light passes through the tissue along a light path from which a first portion of the oscillating light exits the tissue and along which a second portion of the oscillating light is absorbed by the oxygenated blood. The first portion is modulated by a volume of oxygenated blood that is present in said light path. Levels of light are detected near the tissue and a detector signal is created which is related to the detected light levels. The detected light includes at least some of the first portion of oscillating light exiting from the tissue and a secondary light from other sources. The detector signal includes a first component caused by detection of the first portion of oscillating light exiting the tissue, and a second component caused by the detection of the secondary light. The detector signal is filtered to attenuate at least a part of the second component of the detector signal and to pass the first component of the detector signal substantially un-attenuated. At least one characteristic relating to the person is determined based on a volume of oxygenated blood in the light path through the tissue as characterized by the modulation of the first component of the detector signal.

Another embodiment involves a blood oxygen sensor for determining at least one circulatory related characteristic of a person that includes an oscillating light generator for generating an oscillating light having an intensity that oscillates at an oscillating light frequency. The oscillating light includes an electromagnetic wavelength which causes the oscillating light to be absorbed by tissue of the person in amounts that are proportional to a volume of oxygenated blood in some tissue toward which the oscillating light is directed. A light directing apparatus is used for directing the oscillating light toward the tissue of the person to cause the oscillating light to enter the tissue and pass through the tissue along a light path from which a first portion of the oscillating light exits the tissue and along which a second portion of the light is absorbed by the oxygenated blood in the light path such that the first portion is modulated by a volume of oxygenated blood that is present in said light path. A light detector detects levels of light near the tissue in a spaced apart relationship to the light directing apparatus. The light detector also creates a detector signal which is related to the detected light levels. The detected light includes at least some of the first portion of oscillating light exiting from the tissue and a secondary light from sources other than the oscillating light generator. The detector signal includes a first component caused by detection of the first portion of oscillating light exiting the tissue, and a second component caused by the detection of the secondary light. A filter is included for filtering the detector signal to attenuate at least part of the second component of the detector signal and to pass the first component of the detector signal substantially un-attenuated. A computing device is also included for receiving the filtered detector signal and for determining one or more characteristics relating to the person based on a volume of oxygenated blood in the light path through the tissue as characterized by the modulation of the first component of the detector signal.

Yet another embodiment involves a method for determining at least one circulatory related characteristic of a person in which light is generated at a wavelength which causes the light to be absorbed by tissue of the person in amounts that are proportional to a volume of oxygenated blood in some tissue towards which the light is directed. The light is directed towards the tissue of the person to cause the light to enter the tissue. The light is guided to cause the light to pass through the tissue along a light path which includes the light entering and exiting the tissue a plurality of times. A first portion of the light exits the tissue and a second portion of the light is absorbed by the oxygenated blood in the light path such that the first portion is modulated by a volume of oxygenated blood that is present in the light path. Levels of light are detected near the tissue after the light has passed through the light path and a detector signal is created which is related to the detected light levels. The detected light includes at least some of the first portion of light exiting from the tissue and a secondary light from other sources. The detector signal includes a first component caused by detection of a first portion of light exiting the tissue, and a second component caused by the detection of the secondary light. At least one characteristic relating to the person is determined based on a volume of oxygenated blood in the light path through the tissue as characterized by the modulation of the first component of the detector signal.

Still another embodiment involves a blood oxygen sensor for determining at least one circulatory related characteristic of a person which includes a light generator for generating a light at a wavelength which causes the light to be absorbed by tissue of the person in amounts that are proportional to a volume of oxygenated blood in some tissue toward which the light is directed. A light directing apparatus is included for directing the light toward the tissue of the person to cause the light to enter the tissue. A light guide guides the light to pass through the tissue along a light path which includes the light entering and exiting the tissue a plurality of times. A first portion of the light exits the tissue and a second portion of the light is absorbed by the oxygenated blood in the light path such that the first portion is modulated by a volume of oxygenated blood that is present in the light path. A light detector detects levels of light near the light guide which includes at least some of the first portion of light exiting from the tissue. The light detector creates a detector signal which is related to the detected light levels. A computing device receives the detector signal and determines one or more characteristics relating to the person based on a volume of oxygenated blood in the light path through the tissue as characterized by the modulation of the first portion of the light exiting the tissue.

In addition to the exemplary aspects and embodiments described above, further aspects and embodiments will become apparent by reference to the drawings and by study of the following descriptions.

DETAILED DESCRIPTION

Figure 1:
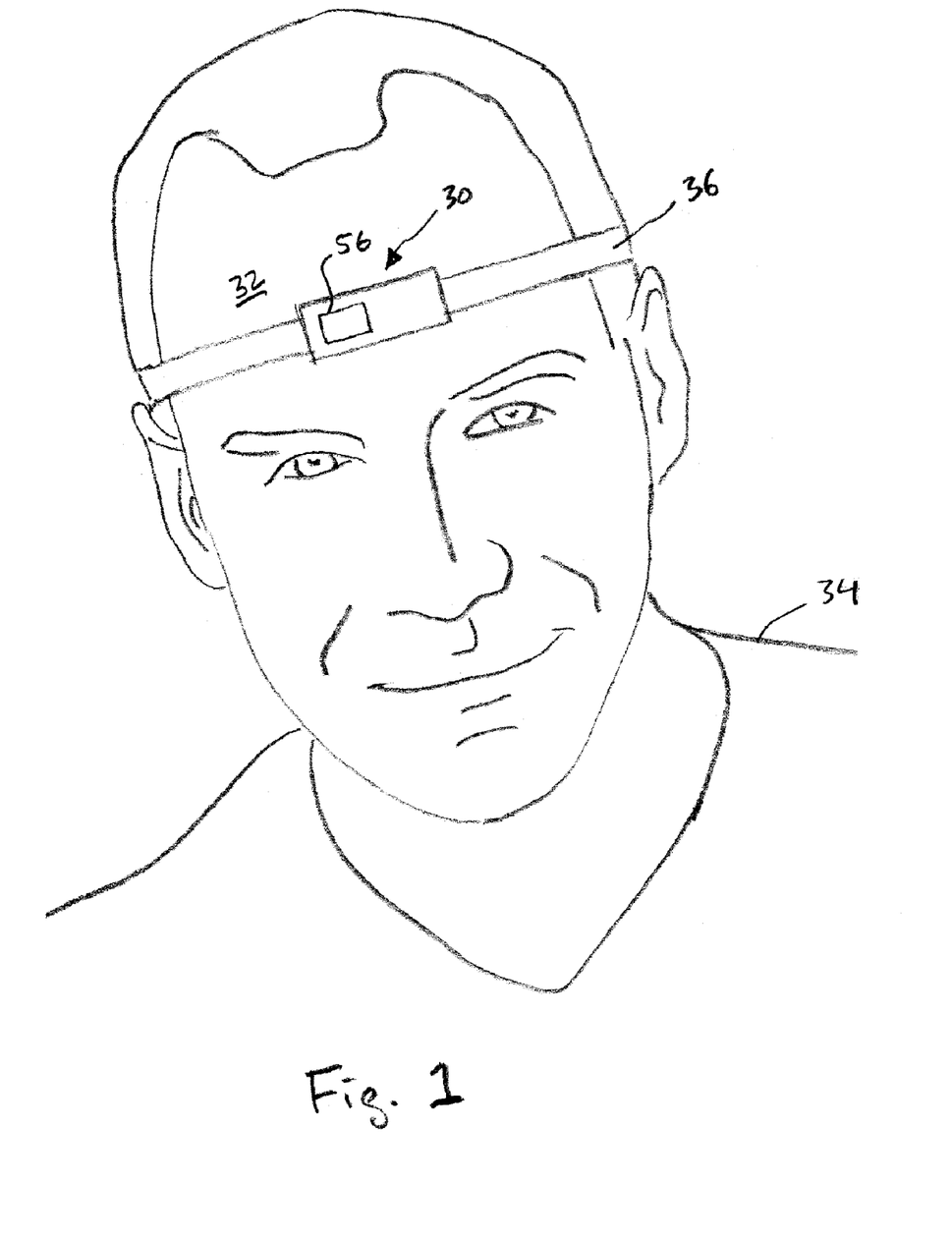
FIG. 1 is a perspective view of blood oxygen sensing device as described herein, attached to a head of a person for reading blood oxygen in tissue of the person.

A blood oxygen sensor 30 for determining a volume of oxygenated blood in tissue 32 of a person 34 is shown in FIG. 1 attached to the forehead of the person with a band 36 at a position that is centered on or slightly offset from a vertical center of the person's forehead. Sensor 30 measures circulatory related characteristics of the person, and in the present example, displays an indication of the characteristic on a display 56. One example of these characteristics is changes in the volume of blood pumped by each heart beat in the tissue of the forehead. Each time that the heart beats, oxygenated blood is pumped into the arteries and out to tissue 32 in the forehead. With each beat, the pressure inside of the capillaries increases and the capillaries expand in volume with the blood. Between the heart beats, the blood flows from the capillaries into the blood vessels which decreases the volume of blood in the tissue. Sensor 30 can also be used on other tissue of the person and can be attached to the person in other ways.

Blood oxygen sensor 30 uses light at a substantially single wavelength to determine the blood oxygen and circulatory related characteristics of the person while reducing or eliminating the adverse effects of other secondary light sources, movement of the person or sensor during the use as well as other issues associated with traditional sensors.

In one embodiment, blood oxygen sensor 30 utilizes an oscillating oxygen sensing light 38 that is oscillated in level or intensity to determine circulatory related characteristics of the person, including for example, blood oxygen level, heart rate, breathing rate and the relative volume of blood in the tissue at any given time. Oscillating light 38 is generated at an electromagnetic wavelength frequency that is absorbed by oxygenated blood, for example in a range of 800-900 nanometers (nm) for instance 850 nm. The intensity of the oscillating light is oscillated at a frequency of about 3.2 kilo-Hertz in the present example. Other frequencies can also be used so long as the frequency is different than frequencies common to sources of noise external light, such as 60 Hz which is common in incandescent lights. Frequencies above about 120 Hz are generally considered to be suitable.

Oscillating light 38 is directed into the tissue and the oscillating light passes through and emerges from or exits the tissue where the light is detected. Oscillating light 38 travels along a light path between points where the light is generated and where the light is detected. The oscillating light on the path also passes through the tissue of the person where the light enters the tissue and exits the tissue at least once. In some circumstances, the light enters and exits the tissue multiple times along the light path which increases the amount of blood encountered by the oscillating light. Some portion of the oscillating light is absorbed by oxygenated blood and another portion of the oscillating light exits the tissue where it is detected. The amount of oscillating light absorbed is related to the level of oxygen in the blood.

Once the portion of the oscillating light exiting the tissue is detected, a detector signal is created that is related to the detected light levels. In some circumstances, secondary light other than the oscillating light is detected along with the oscillating light exiting the tissue. The secondary light can be from external from sources other than blood oxygen sensor 30, or from other sources in sensor 30, or a combination of both. The detector signal includes a first component that is caused by the detection of the portion of the oscillating light exiting the tissue and a second component caused by the detection of the secondary light.

The detector signal is filtered to attenuate at least a portion of the second component and to pass the first component substantially without attenuation. The first component of the oscillating light can be considered to be modulated at the oscillation frequency. The filtering removes components of the detector signal that are related to environmental noise at lower frequencies, such as fluorescent light, while passing the oscillating light. The first component is then used for determining at least one circulatory characteristic of the person. An inverse relationship exists between the first portion of oscillating light exiting the tissue and the second portion of oscillating light absorbed by the oxygenated blood. Because of this, more oscillating light exiting the tissue means that less of the oscillating light has been absorbed by oxygenated blood. On the other hand, less oscillating light exiting the tissue means that more of the oscillating light has been absorbed by oxygenated blood. Accordingly, more detected oscillating light means that there is a lower level of oxygenated blood in the light path, while less detected oscillating light means that there is a higher level of oxygenated blood in the light path.

Figure 2:
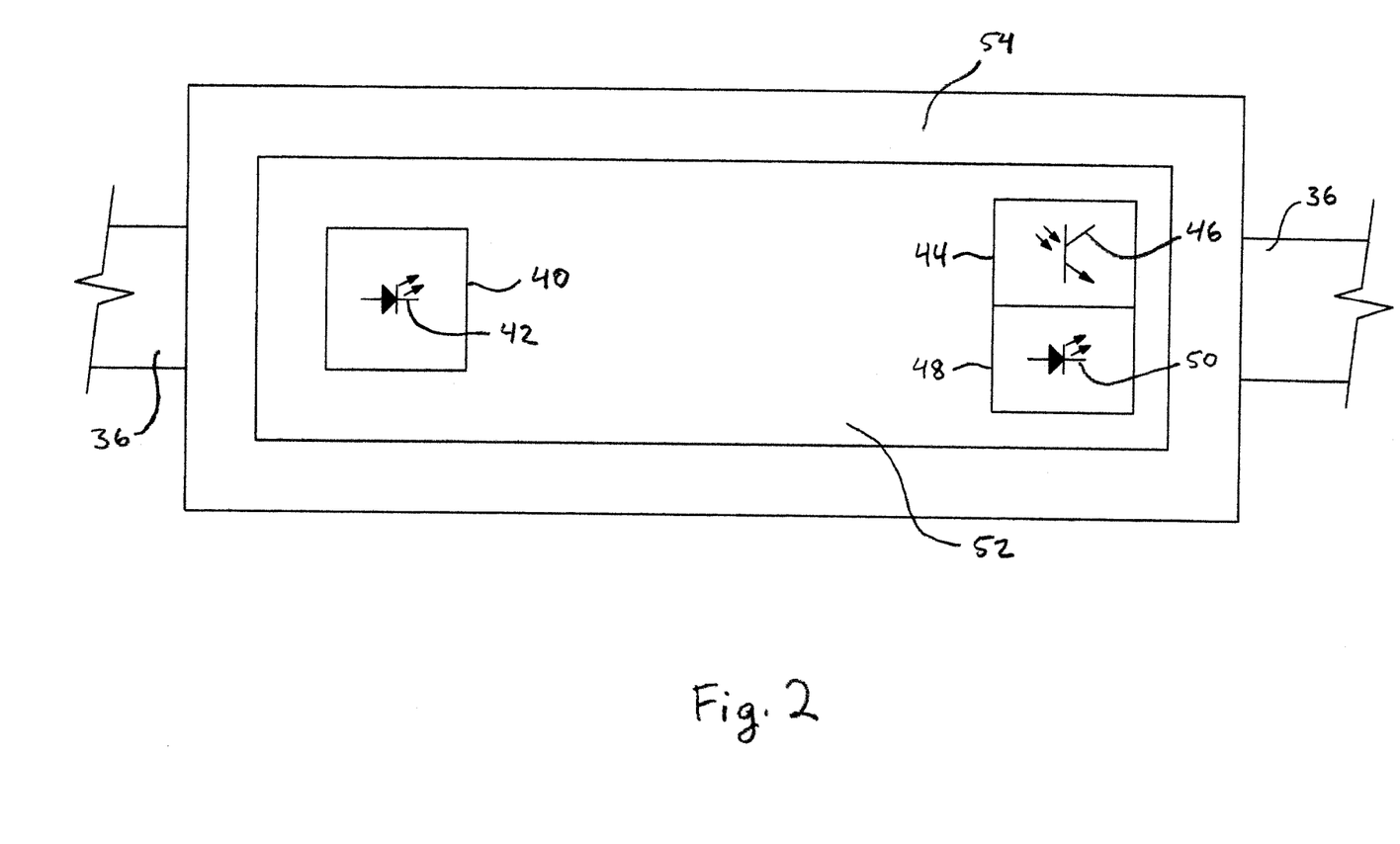
FIG. 2 is a diagrammatic view of a sensor mount of the blood sensing device shown in FIG. 1 showing an oscillating light source, a bias light source and a photosensor.

Sensor 30, shown in FIG. 2, includes a light generator 40 having a light source 42 for generating oscillating light 38 at the wavelength that is absorbed by the oxygenated blood. A light detector 44 having a light sensor 46 is arranged to receive oscillating light 38 (FIG. 3) generated by the light generator 40. A bias light driver 48 includes a bias light source 50 that is positioned adjacent to light sensor 46. Bias light driver 48 and bias light source 50 are discussed in more detail below. Light sensor 46 is positioned in a spaced apart relationship with light source 42. In the present example, light sensor 46 and light source 42 are spaced about 0.75 inches apart. Other spacing is also suitable such as between 0.5 and 1 inches depending on light intensity levels, skin pigmentation or other factors.

A light reflector 52 is arranged to surround light source 42, light sensor 46, and bias light source 50 as well as to include the space between light source 42 and light sensor 46. Light reflector 52 can be made of an infrared (IR) reflective material. Light reflector 52 can be surrounded by light absorber 54 that is made of an IR absorbing material. Light reflector 52 serves as a light pipe or light guide to guide oscillating light 38 through the tissue of the person as will be described immediately hereinafter.

Figure 3:
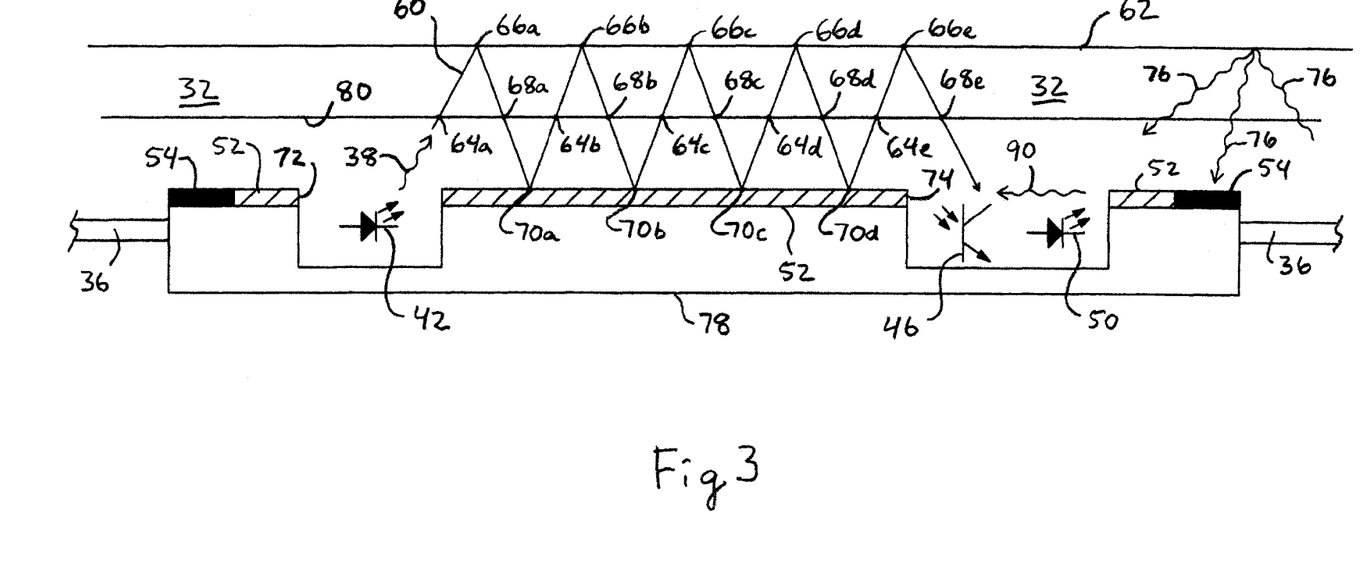
FIG. 3 is diagrammatic cross section view of the sensor mount shown in FIG. 2 and a portion of the person's head.

As shown in the cross section view in FIG. 3, light reflector 52 guides oscillating light 38 along light path 60. Light path 60 shown in FIG. 3 is diagrammatic in nature so as to illustrate certain concepts. In practical application, the oscillating light will travel through the tissue on several different paths which may be collectively referred to herein as the light path. In the example shown in FIG. 3, light source 42 generates and directs oscillating light 38 into tissue 32 between light reflector 52 and skull bone 62 (illustrated as a line for purposes of simplicity) of person 34 through an opening 72 in light reflector 52. The oscillating light enters the tissue near light source 42 at point 64a and travels through the tissue to the skull. Skull 62 reflects the oscillating light, as shown in FIG. 3 at point 66a which causes the oscillating light to pass through more tissue toward the exterior of the tissue where the oscillating light exits the tissue at point 68a. The oscillating light is then reflected off of light reflector 52 at point 70a which redirects the oscillating light back into the tissue at point 64b. At this point the process is generally repeated through points 64b-e to 70b-d along light path 60 until the oscillating light exits the tissue at point 68e and the oscillating light passes through opening 74 in light reflector 52 where the oscillating light reaches light sensor 46.

Light reflector 52 acts as a light pipe to guide the oscillating light from light source 42 through the tissue multiple times before the oscillating light is detected. By guiding the oscillating light in this way, light reflector 52 causes the oscillating light to pass through more tissue than traditional blood oxygen sensors; this increases the amount of blood encountered by the oscillating light and increases the amount of oscillating light absorbed by oxygen in the blood.

Light absorber 54, FIGS. 2 and 3, is used to absorb external secondary light 76 that comes from sources external to blood oxygen sensor 30 in order to reduce or prevent the external secondary light 76 from reaching light sensor 46. External secondary light 76 acts as uncontrolled interference or noise reaching sensor 30 and therefore should be minimized. Light absorber 54 can absorb light at all of the frequencies to which light sensor 46 responds. An outer surface 78 can be made of an opaque material that blocks external light of all frequencies.

In the present example, sensor 30 is mounted with the light source 42 and light sensor 46 facing toward the forehead of person 34 in an area where there is no hair. The example shown in FIG. 3 shows sensor 30 a short distance from the forehead of the person to illustrate the operation of sensor 30. It is not necessary for sensor 30 to contact skin surface 80 of the person to operate, although sensor 30 is also operable when in contact with the skin surface. In the present example, sensor 30 is mounted in a way which maintains a constant distance from the skin of the person. To accomplish this, sensor 30 can include materials which allow the sensor to flex in order to conform to the contours of the person's skin or tissue. The constant distance between the sensor and the skin of the person may be maintained in other ways as well.

Bias light driver 48 includes bias light source 50 which is positioned adjacent to light sensor 46 in the examples shown in FIGS. 2 and 3. Bias light driver 48, (FIGS. 2 and 5), generates a bias light 90 that is used in compensating for external secondary light 76. Bias light 90 couples to light sensor 46 and combines with the portion of external secondary light 76 that is sensed by light sensor 46 and is customized to create a constant target level of secondary light at light sensor 46.

Light sensor 46, in the present example, is a type of optical detector which has a non-linear response. The response of light sensor 46 to oscillating light 38 is a function of secondary light. External secondary light 76 typically contains unwanted noise from several sources which adds unwanted noise to the measurement of oscillating light 38. As will be seen, sensor 30 determines the level of external secondary light 76 and uses bias light 90 as an additional secondary light to bring the total secondary light up to a target operating level that is higher than any external secondary light expected during normal operation of sensor 30. By bringing the total secondary light up to the target operating level, light sensor 46 is biased into an operating range that is generally linear.

Attention is now directed to the manner in which sensor 30 compensates for variations in external secondary light 76. Light sensor 46 generates a detector signal 124 (FIG. 6) in response to the detection of the total secondary light (external secondary light 76 and bias light 90) and oscillating light 38. Since the external secondary light is generated by ambient noise, which typically oscillates in intensity below 120 Hz, total secondary light is also relatively low frequency compared with the oscillating light 38 which is modulated at a relatively higher frequency. As will be seen, detector signal 124 is band pass filtered to pass signals resulting from the detection of the oscillating light while blocking signals resulting from the secondary light. The resulting filtered signal is used for determining the circulatory related characteristics of the person.

Circuit diagrams in FIGS. 4-8 are illustrative of one embodiment which incorporates several different concepts. Power sources for circuitry in blood oxygen sensor 30 can be derived from portable power sources, such as batteries, or from a fixed source such as from an electric utility company. Power is provided for the circuitry in a manner that is known to those skilled in the art of circuit design. In the present examples, V1 is ground, V2 is approximately 1.65 volts and V3 is approximately 3.3 volts.

Figure 4:
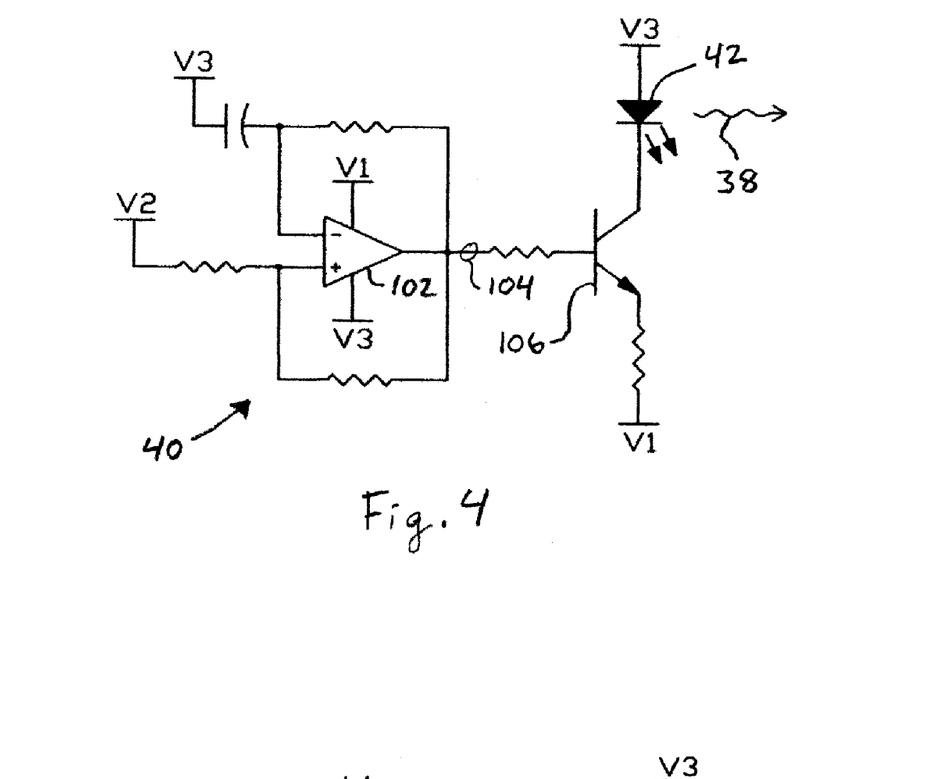
FIG. 4 is a diagram of an oscillating light generator.

Light generator 40 is shown in FIG. 4 along with light source 42 and oscillating light 38. Light generator 40 includes an op amp 102 that is configured as an oscillator to provide an oscillating output signal 104 at a frequency of 3.2 kHz between a low voltage state and a high voltage state. Oscillating output signal 104 controls a transistor 106 which is connected to light source 42. Light source 42 is in this instance an infra-red LED that produces infra-red light in response to current flow and turns off when no current is flowing through transistor 106. Current flows through transistor 106 between V3 and V1 when oscillating output signal 104 is in the high voltage state. In response, light source 42 produces oscillating light 38 with a generally square wave. Current does not flow through transistor 106 when oscillating signal 104 is in the low voltage state and this causes light source 42 to not produce oscillating light 38. In this way light generator 40 produces oscillating light 38 with an oscillating intensity.

Figure 5:
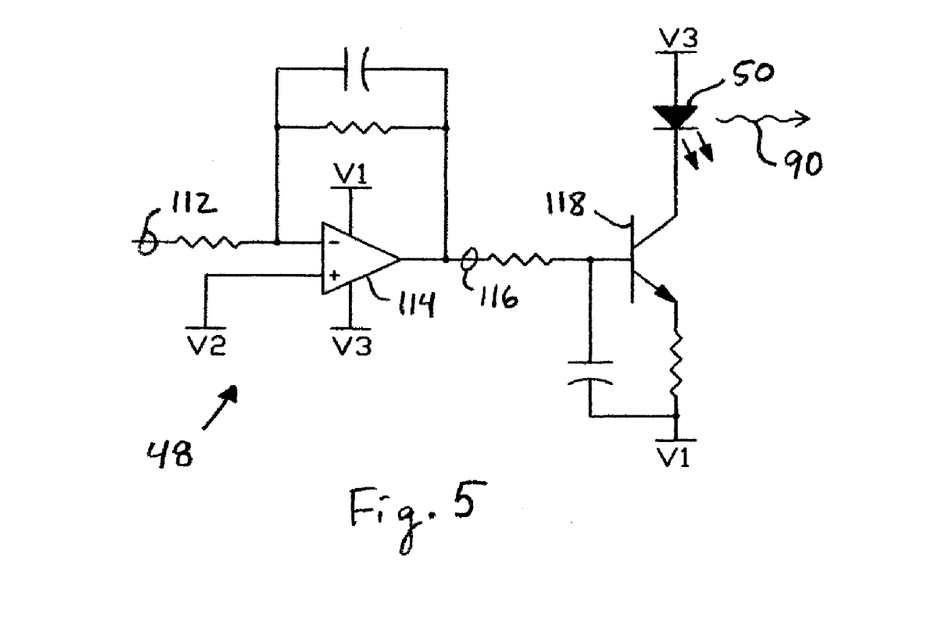
FIG. 5 is a diagram of a bias light source.

One embodiment of bias light driver 48 is shown in FIG. 5. Bias light driver 48 receives a reference signal 112 from light detector 44 and generates bias light 90 from bias light source 50 in response. The generation of reference signal 112 will be described in further detail below, but for the moment, it is sufficient to understand that this signal is related to the levels of light received at light sensor 46. Bias light driver 48, in the present example, is configured to include a low pass filter that removes signals resulting from the oscillation of oscillating light 38. This causes a bias source op amp 114 to create output signal 116 that is inversely proportional to the amount of secondary light detected by light detector 44. In other words, larger amounts of secondary light sensed by light detector 44 result in a smaller output signal 116 and smaller amounts of secondary light sensed by light detector 44 result in a larger output signal 116. Bias light driver 48 uses output signal 116 to control a bias transistor 118 which supplies current to bias light source 50. In this way, bias light driver 48 produces bias light 90 at a level that causes the total level of the secondary light to be at a target level.

Figure 6:
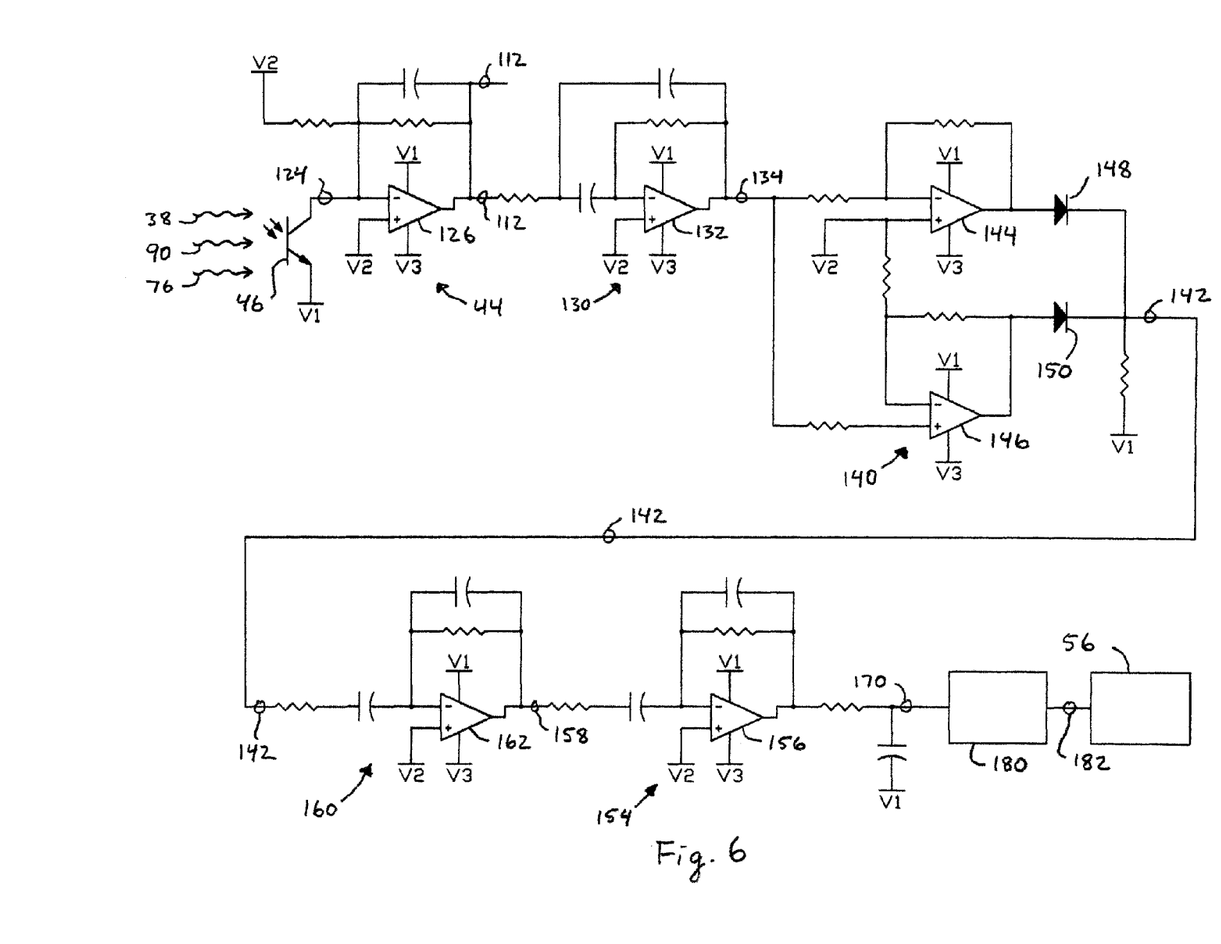
FIG. 6 is a diagram of a light detector, filtering sections and an absolute value section.

Light detector 44 is shown in FIG. 6 along with circuitry used in producing the circulatory related signals. A portion of light 38 that is not absorbed by oxygenated blood along path 60 is received by light sensor 46 along with secondary bias light 90 and external secondary light 76. Light sensor 46 generates a detector current 124 in response to the light received. Detector current 124 is one example of a detector signal in which the signal is generally unmodified. Other detector signals are also discussed with each one having some processing, manipulation or filtering. Light detector 44 includes an op amp 126 that is configured for converting detector current 124 into a voltage that is reference signal 112. Light detector 44 is connected to a first filter stage 130 which includes an op amp that is configured as a band pass filter. First filter stage 130 operates to pass signals that are within a certain band that includes 3.2 kHz, in the present example, while attenuating lower frequencies such as those in the frequencies of external secondary light 76. First filter stage 130 also amplifies signals within the pass band and generates a pass band signal 134.

An absolute value section 140 receives pass band signal 134 and generates an absolute value signal 142. Absolute value signal 142 is an absolute value representation and amplification of pass band signal 134. Positive and negative components of pass band signal 134 can be amplified by different amounts using absolute value section 140. Absolute value section 142 includes first and second op amps 144 and 146 used for amplification and diodes 148 and 150 used for rectification.

In one embodiment, the positive component of pass band signal 134 is amplified more than the negative component of pass band signal 134. This can be considered as asymmetric amplification. In further examples, the positive component is amplified three or four times as much as the negative component. Amplification of the positive and negative components of pass band signal 134 to different degrees extends the range of pass band signals that can be used. In the case of a large pass band signal, the positive component of the signal saturates during the positive half of the cycle while the inverted negative component is in a linear range. In the case of a small pass band signal, the positive component of the signal is in the linear range while the inverted negative component is very small. In the case of a medium size pass band signal, both the positive and the negative components of the pass band signal are in the linear range. Absolute value section 140 therefore extends the range of signals that are usable on both the small and large ends of pass band signals. Among other things, this allows blood oxygen sensor 30 to be poorly situated on the person while still providing a robust measurement.

Second filter stage 160 includes an op amp 162 that is configured as a band pass filter to receive and filter and amplify absolute value signal 142 and to produce second filter stage signal 158. A third filter stage 154 includes an op amp 156 that is also configured as a band pass filter. Filter stage 154 further amplifies the signal while attenuating higher and lower frequency components. Filter stage 154 produces blood oxygen signal 170.

Blood oxygen signal 170 contains information about the volume of blood in tissue 32 (FIG. 3) at a given time because the absorption of oscillating light 38 is proportional to the volume of oxygenated red blood cells in path 60.

Pulse rate can be determined by determining heart beats by increases in oxygen levels in the blood and then determining how many beats occur per minute. Blood oxygen signal 170 can be low pass filtered at about 20 Hz for determining the timing and shape within the heart beat. For determining the heart beat spacing blood oxygen signal 170 can be low pass filtered at about 2 Hz.

Blood oxygen sensor 30 can also be used for determining breathing. Breathing modulates the frequency and amplitude of the heart rate. For example, breathing can vary the heart rate as much as 10%. Breathing can be detected by blood oxygen sensor 30 as relatively low amplitude increases and decreases in blood oxygen levels. The resolution of the present blood oxygen sensor 30 allows the determination of the breathing rate where traditional blood oxygen sensors have failed. Information about breathing rate can be related to emotional state and emotional responses of the person. Emotional state can also be detected as constrictions in blood flow.

Although the present blood oxygen sensor has been described in detail using an oscillating light source, the light directing or guiding apparatus (or light reflector and absorber) and bias light concepts described herein can be used with one or more non-oscillating light sources. Sensors with non-oscillating light sources also benefit from passing through tissue multiple times as is accomplished by using the light guiding apparatus, and also benefit by having a light level that is biased into the linear range of the light detector.

Detector current 124 or other signals can be converted to digital and processed thereafter in the digital format, including filtering. Digital processing of these signals minimizes the impact of noise. An exemplary computing device 180, shown in FIG. 6, converts blood oxygen signal 170 into digital format and provides a display signal 182 to display 56. Computing device 180 can be used for other types of processing as well.

The circulatory information determined by blood oxygen sensor can be displayed for viewing by the person or a health care professional. Sensor 30 can include wired or wireless communication to a display device, either integral to the sensor, or separate. Sensor 30 can also be connected to a computing device for storage of the information or for further processing and/or display. In one instance, the circulatory related information can be used The information can also be used in systems for determining mental state of the person alone or in conjunction with other sensors.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A blood oxygen sensor comprising:
an oscillating light generator to generate an oscillating light having an electromagnetic wavelength absorbable by a tissue of a person in an amount proportional to a volume of oxygenated blood in the tissue such that a first portion of the oscillating light exits the tissue and a second portion of the light is absorbed by the oxygenated blood;
a light detector to detect a level of light near the tissue and to create a detector signal related to the detected light level, wherein the detected level includes a first detected component comprising at least some of the first portion of the oscillating light exiting the tissue and a second detected component comprising external secondary light;
a bias light source to generate bias light to combine with the second detected component, wherein the bias light varies in proportion to the second detected component;
a filter to attenuate at least part of the second detected component and the bias light and to pass the first detected component of the detector signal substantially un-attenuated;
a memory having machine readable instructions stored therein; and
a processor which, when executing the machine readable instructions, determines the volume of oxygenated blood based on the first detected component and determines circulatory characteristic relating to the person based on the volume of oxygenated blood.

2. A blood oxygen sensor as defined in claim 1, further comprising a light guide between the oscillating light generator and the light detector to reflect oscillating light exiting from the tissue back into the tissue.

3. A blood oxygen sensor as defined in claim 2 wherein the light guide includes a reflective surface.

4. A blood oxygen sensor as defined in claim 2 wherein the light guide includes an opaque portion to absorb at least a portion of the second detected component.

5. A blood oxygen sensor as defined in claim 1 wherein the processor when executing the instructions determines the circulatory characteristic based on an inverse relationship between the first portion and the second portion.

6. A blood oxygen sensor as defined in claim 1 wherein the electromagnetic wavelength is substantially constant.

7. A blood oxygen sensor as defined in claim 6 wherein the wavelength is about 850 nm.

8. A blood oxygen sensor as defined in claim 1 wherein the oscillating light has a frequency above 120 Hz.

9. A blood oxygen sensor as defined in claim 8 wherein the oscillating light has a frequency of about 3.2 kHz.

10. A blood oxygen sensor as defined in claim 1 wherein the oscillating light generator is to oscillate the light by turning a light source on and off.

11. A blood oxygen sensor as defined in claim 1 wherein the light detector is to operate in a linear range when detecting the level of light.

12. A blood oxygen sensor as defined in claim 11, wherein the bias light is to bias the light detector to operate in a linear range.

13. A blood oxygen sensor as defined in claim 1 wherein the processor determines a breathing rate from the first component.

14. A blood oxygen sensor as defined in claim 1 wherein the processor determines a heart rate from the first component.

15. A blood oxygen sensor as defined in claim 14, further comprising an asymmetric amplifier to asymmetrically amplify the first component of the detector signal to extend a range of detector signals used to determine the heart rate.

16. A blood oxygen sensor as defined in claim 15 wherein the asymmetric amplifier is to amplify positive portions of the first detected component of the detector signal about four times as much as negative portions of the first detected component of the detector signal.

17. A blood oxygen sensor as defined in claim 1 wherein at least part of the filter is integrated with the processor.

18. A blood oxygen sensor as defined in claim 1, wherein the blood oxygen sensor is structured to be positioned on a forehead so the tissue through which the oscillating light is to travel is the forehead.

19. A blood oxygen sensor as defined in claim 18, wherein the blood oxygen sensor is structured to be positioned offset from a vertical center of the forehead.

20. A blood oxygen sensor as defined in claim 1 further comprising a display to display an indication of the circulatory characteristic.

21. A blood oxygen sensor as defined in claim 1, wherein the circulatory characteristic is a relative volume of blood in the tissue.

22. A blood oxygen sensor as defined in claim 1, wherein the bias light source is adjacent to the light detector.

23. A blood oxygen sensor as defined in claim 1, wherein the oscillating light generator and the light detector are separated a distance of about 0.5 inches to about 1.0 inch.

24. A blood oxygen sensor as defined in claim 23, wherein the oscillating light generator and the light detector are separated a distance of about 0.75 inches.

25. A blood oxygen sensor as defined in claim 1, wherein the light generator and the light detector are separated a distance determined based on an amount of skin pigmentation of the person.

26. A blood oxygen sensor as defined in claim 2, wherein the light guide comprises a light reflector surrounded by a light absorber, wherein the light reflector reflects the first component and the light absorber absorbs the second component.

27. A blood oxygen sensor as defined in claim 1, wherein the blood oxygen sensor is structured to be located such that the oscillating light is to travel through the tissue in a plurality of paths.

28. A blood oxygen sensor as defined in claim 1, wherein the blood oxygen sensor is structured to be positioned in contact with a skin surface.

29. A blood oxygen sensor as defined in claim 28, wherein the blood oxygen sensor is flexible to conform to a contour of the skin surface.

30. A blood oxygen sensor as defined in claim 1, wherein an amount of the bias light is to change based on a change in an amount of the second detected component to maintain a substantially constant combination of the bias light and the second detected component.

31. A blood oxygen sensor as defined in claim 1, wherein a bias light driver, which includes the bias light source, is to receive a signal from the light detector indicative of an amount of the second detected component.

32. A blood oxygen sensor as defined in claim 1, wherein an amount of the bias light is inversely proportional to an amount of the second detected component.

33. A blood oxygen sensor as defined in claim 1, wherein the sensor is structured to maintain a constant distance between a skin surface of the person and the sensor.

34. A blood oxygen sensor as defined in claim 1, wherein the bias light source is housed in the sensor.

35. A blood oxygen sensor as defined in claim 1, wherein the bias light source is incorporated into a bias light driver that includes a low pass filter to remove one or more signals resulting from the oscillation of oscillating light.

36. A blood oxygen sensor as defined in claim 1, wherein the oscillating light generator is to pulsate the oscillating light at a frequency.

37. A blood oxygen sensor comprising:
   a light generator to generate light at a wavelength absorbable by a tissue of a person in an amount proportional to a volume of oxygenated blood in the tissue;
   a light guide to guide the light through the tissue along a light path which includes the light entering and exiting the tissue a plurality of times, a first portion of the light exiting the tissue and a second portion of the light being absorbed by the volume of oxygenated blood in the light path;
   a light detector to detect a level of light near the light guide and to create a detector signal related to the detected light level, wherein the detected level includes a first detected component comprising at least some of the first portion of the light exiting the tissue and a second detected component comprising external secondary light;
   a bias light source to generate bias light to combine with the second detected component, wherein the bias light is in proportion to the second detected component;
   a filter to attenuate at least part of the second detected component and the bias light and to pass the first detected component of the detector signal substantially un-attenuated;
   a memory having machine readable instructions stored therein; and
   a computing device which, when executing the machine readable instructions, determines the volume of oxygenated blood based on the first detected component and determines a circulatory characteristic based on the volume of oxygenated blood.

38. A blood oxygen sensor as defined in claim 37, wherein the light guide is to reflect light exiting the tissue back into the tissue at least once.

39. A blood oxygen sensor as defined in claim 37, wherein the light is to reflect off of a bone of the person.

40. A blood oxygen sensor as defined in claim 39 wherein the light is to reflect off a skull.

41. A blood oxygen sensor as defined in claim 37, wherein the bias light source is to bias the detector into a linear range.

42. A blood oxygen sensor as defined in claim 41, wherein the light guide is to reflect light exiting the tissue back into the tissue at least once.

43. A blood oxygen sensor as defined in claim 37, further comprising a flexible light blocker to conform to a contour of the tissue of the person and at least partially block the second detected component from reaching the light detector.

44. A blood oxygen sensor as defined in claim 37 wherein the detector signal is amplified asymmetrically.

* * * * *